(12) United States Patent
Mark et al.

(10) Patent No.: US 7,347,829 B2
(45) Date of Patent: Mar. 25, 2008

(54) INTRODUCTION SYSTEM FOR MINIMALLY INVASIVE SURGICAL INSTRUMENTS

(75) Inventors: Joseph L. Mark, Indianapolis, IN (US); Michael E. Miller, Trafalgar, IN (US); Timothy A. Goedde, Indianapolis, IN (US)

(73) Assignee: Suros Surgical Systems, Inc., Indianapolis, IN (US)

( * ) Notice: Subject to any disclaimer, the term of this patent is extended or adjusted under 35 U.S.C. 154(b) by 523 days.

(21) Appl. No.: 10/649,068

(22) Filed: Aug. 27, 2003

(65) Prior Publication Data
US 2004/0077938 A1 Apr. 22, 2004

Related U.S. Application Data

(60) Provisional application No. 60/416,755, filed on Oct. 7, 2002.

(51) Int. Cl.
*A61B 5/05* (2006.01)

(52) U.S. Cl. ............... 600/567; 600/411; 600/424; 600/431; 600/433; 600/435; 600/564; 606/170

(58) Field of Classification Search ............... 600/411, 600/585, 424, 431, 433, 435, 567; 606/170
See application file for complete search history.

(56) References Cited

U.S. PATENT DOCUMENTS

| | | | |
|---|---|---|---|
| 5,281,197 A | | 1/1994 | Arias et al. |
| 5,289,831 A | | 3/1994 | Bosley |
| 5,647,374 A | | 7/1997 | Cutrer |
| 5,782,764 A | * | 7/1998 | Werne .................. 600/411 |
| 6,161,034 A | | 12/2000 | Burbank et al. |
| 6,213,988 B1 | * | 4/2001 | McIvor et al. .............. 604/264 |
| 6,251,418 B1 | | 6/2001 | Ahern et al. |
| 6,276,661 B1 | * | 8/2001 | Laird .................. 251/61.1 |
| 6,277,107 B1 | * | 8/2001 | Lurie et al. .................. 604/528 |
| 6,280,399 B1 | | 8/2001 | Rossin et al. |
| 6,347,241 B2 | | 2/2002 | Burbank et al. |

(Continued)

FOREIGN PATENT DOCUMENTS

WO WO-WO 98/22022 A1 5/1998

(Continued)

OTHER PUBLICATIONS

International Search Report #PCT/US03/26958 dated Aug. 28, 2003.

*Primary Examiner*—Brian L. Casler
*Assistant Examiner*—Parikha S. Mehta
(74) *Attorney, Agent, or Firm*—Rader, Fishman & Grauer, PLLC (57) ABSTRACT

A medical system is disclosed that includes a cannula, an introducer stylet removably disposed within the cannula and a target confirmation device selectively insertable within the cannula. In an embodiment of the invention, the introducer stylet is configured for insertion into a patient's body. The outer cannula is sized to fit over the introducer stylet and is positionable at least partially within the patient's body after insertion and removal of the introducer stylet. The target confirmation device is insertable into the outer cannula after removal of the introducer stylet and is configured to confirm the position of the outer cannula relative to the target site. A medical procedure using the medical system of the present invention is also disclosed.

38 Claims, 6 Drawing Sheets

U.S. PATENT DOCUMENTS

| | | |
|---|---|---|
| 6,494,844 B1 * | 12/2002 | Van Bladel et al. ........ 600/567 |
| 6,626,849 B2 | 9/2003 | Huitema et al. |
| 6,725,083 B1 | 4/2004 | Burbank et al. |
| 6,863,676 B2 | 3/2005 | Lee et al. |
| 6,869,430 B2 * | 3/2005 | Balbierz et al. .............. 606/41 |
| 2001/0032649 A1 | 10/2001 | Nagano |
| 2002/0016544 A1 | 2/2002 | Hareyama et al. |
| 2002/0082519 A1 | 6/2002 | Miller et al. |
| 2002/0120212 A1 | 8/2002 | Ritchart et al. |
| 2003/0109801 A1 | 6/2003 | Rhad et al. |
| 2003/0109803 A1 | 6/2003 | Huitema et al. |
| 2003/0199753 A1 | 10/2003 | Hibner et al. |
| 2003/0199754 A1 | 10/2003 | Hibner et al. |
| 2003/0199785 A1 | 10/2003 | Hibner et al. |
| 2004/0034280 A1 | 2/2004 | Privltera et al. |
| 2004/0077972 A1 | 4/2004 | Tsonton et al. |
| 2005/0212175 A1 | 9/2005 | Tsonton et al. |
| 2005/0215922 A1 | 9/2005 | Tsonton et al. |
| 2005/0261581 A1 | 11/2005 | Hughes et al. |
| 2005/0277829 A1 | 12/2005 | Tsonton et al. |

FOREIGN PATENT DOCUMENTS

| | | |
|---|---|---|
| WO | WO 9855016 A1 * | 12/1998 |
| WO | WO-WO 01/54763 A2 | 8/2001 |

* cited by examiner

INTRODUCTION SYSTEM FOR MINIMALLY INVASIVE SURGICAL INSTRUMENTS

CROSS REFERENCE TO RELATED APPLICATIONS

This application claims priority to U.S. provisional application No. 60/416,755 filed on Oct. 7, 2002, which is incorporated herein by reference in its entirety.

BACKGROUND OF THE INVENTION

1. Field of the Invention

The present invention relates to the field of medical devices and more invasive surgical instruments and other medical treatments into a patient's body.

2. Description of the Related Art

Medical procedures have advanced to stages where less invasive or minimally invasive surgeries, diagnostic procedures and exploratory procedures have become desired and demanded by patients, physicians, and various medical industry administrators. To meet these demands, improved medical devices and instrumentation have been developed, such as cannulas or micro-cannulas, medical introducers, vacuum assisted biopsy apparatus, and other endoscopic related devices.

In the field of tissue biopsy, minimally invasive biopsy devices have been developed that require only a single insertion point into a patient's body to remove one or more tissue samples. One such biopsy device incorporates a "tube-within-a-tube" design that includes an outer piercing needle having a sharpened distal end and a lateral opening that defines a tissue receiving port. An inner cutting member is slidingly received within the outer piercing needle, which serves to excise tissue that has prolapsed into the tissue receiving port. A vacuum is used to draw the excised tissue into the tissue receiving port and aspirates the excised tissue from the biopsy site once severed.

Exemplary "tube-within-a-tube" biopsy devices are disclosed in pending U.S. patent application Ser. Nos. 09/707,022 and 09/864,031, which are owned by the assignee of the present invention. Among other features, the exemplary biopsy devices can be used in conjunction with Magnetic Resonance Imaging (MRI). This compatibility is due to the fact that many of the components of the biopsy devices are made of materials that do not interfere with operation of MRI apparatus or are otherwise compatible therewith. It is desirable to perform biopsies in conjunction with MRI because it is currently the only non-invasive visualization modality capable of defining the margins of a tumor.

While the exemplary MRI compatible biopsy devices have proven effective in operation, in some procedures it is desirable to create a pathway to the biopsy site for precise introduction of the biopsy device and other medical treatments into the patient. For these and other reasons, an MRI compatible medical introduction system is desirable for use with minimally invasive biopsy devices, such as those employing a "tube-within-a-tube" design.

SUMMARY OF THE INVENTION

A medical system is disclosed that includes a cannula, an introducer stylet removably disposed within the cannula and a target confirmation device selectively insertable within the cannula. In an embodiment, the introducer stylet is configured for insertion into a patient's body. The outer cannula is sized to fit over the introducer stylet and is positionable at least partially within the patient's body after insertion and removal of the introducer stylet. A target confirmation device is insertable into the outer cannula after removal of the introducer stylet and is configured to confirm the position of the outer cannula relative to the target site. A medical procedure using the medical system of the present invention is also disclosed.

BRIEF DESCRIPTION OF THE DRAWINGS

Embodiments of the invention will now be described, by way of example, with reference to the accompanying drawings, wherein.

DETAILED DESCRIPTION

Referring now to the drawings, the preferred illustrative embodiments of the present invention are shown in detail. Although the drawings represent some preferred embodiments of the present invention, the drawings are not necessarily to scale and certain features may be exaggerated to better illustrate and explain the present invention. Further, the embodiments set forth herein are not intended to be exhaustive or otherwise limit or restrict the invention to the precise forms and configurations shown in the drawings and disclosed in the following detailed description.

Figure 1:
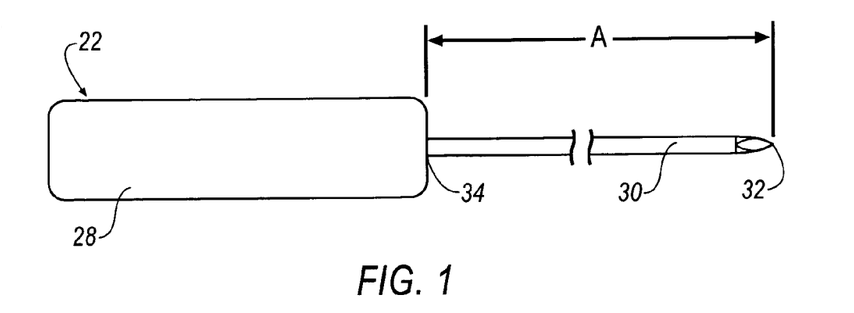
FIG. 1 is a side view of an introducer stylet according to an embodiment of the present invention.
Figure 2:
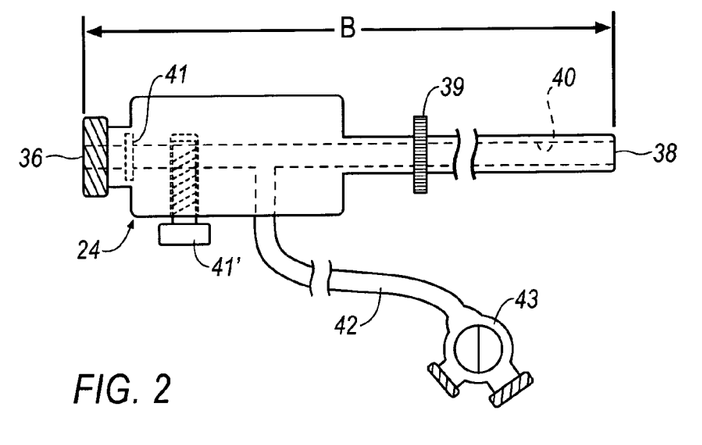
FIG. 2 is side view of an outer cannula and fluid conduit according to an embodiment of the present invention.
Figure 3:
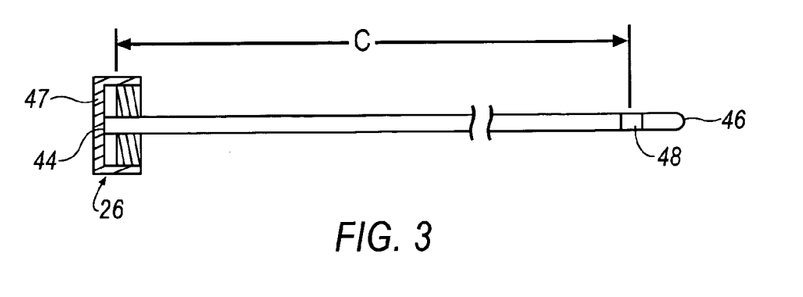
FIG. 3 is a side view of a target confirmation device according to an embodiment of the present invention.

Referring to FIGS. 1-3, a medical system 20 is shown that includes an introducer stylet 22, an outer cannula 24 and a target confirmation device 26. As will be described in detail, system 20 is particularly, but not necessarily, suited for use in biopsy procedures that identify the target biopsy site using Magnetic Resonance Imaging (MRI) or comparable medical imaging modality.

In an embodiment, introducer stylet 22 includes a handle 28 and a stylet 30 having a distal end 32 and a proximal end 34 connected to handle 28. Handle 28 may be made of a medical grade resin or other MRI compatible material. Stylet 30 may also be made of an MRI compatible, medical grade material, such as 316 stainless steel or inconel 625.

In a particular configuration, a distal end 32 of stylet 30 includes a tissue piercing tip, such as a trocar tip, to facilitate penetration of stylet 30 into a patient's tissue. In addition to a trocar tip, it will be appreciated that stylet 30 may include other devices for of piercing the patient's tissue, including without limitation, devices that use a laser or radio frequencies (RF) to pierce the tissue. The length of stylet 30 is generally denoted by the reference character "A" in FIG. 1.

Referring to the embodiment shown in FIG. 2, outer cannula 24 extends from an open proximal end 36 to an open distal end 38, which is separated from proximal end 36 by a distance "B." Like introducer stylet 30, outer cannula 24 may be made from a medical grade resin or other MRI compatible material. In some configurations, proximal end 36 may include a luer-style fitting or other suitable configuration for interfacing, but not necessarily connecting, outer cannula 24 with target confirmation device 26. A depth limiting member 39, such as a rubber o-ring, may be moveably disposed on outer cannula 24 to limit the insertion depth of outer cannula 24 into the patient's body.

In an embodiment, outer cannula 24 also includes an inner lumen 40 therethrough, which is open to communication with a fluid conduit 42 for supplying fluids, such as saline and anesthetics, or removing fluids, such as blood, from the patient's body. Fluid conduit 42 communicates with inner lumen 40 via a port in outer cannula 24. In some configurations, outer cannula 24 may include a haemostatic valve, depicted generally as element 41, or a manually operable valve 41' that can be selectively closed to prevent the escape of fluid from proximal end 36. Fluid conduit 42 may also include a directional valve 43 to selectively control the supply and removal of fluid to and from inner lumen 40, respectively.

In the embodiment shown in FIG. 3, target confirmation device 26 is an elongated member that is sized to fit within inner lumen 40 of outer cannula 24. Target confirmation device 26, which may be made of a medical grade resin or other MRI compatible material, extends from a connecting end 44 to a distal end 46. Connecting end 44 may be configured with a cap 47 that abuts outer cannula 24. In some configurations, cap 47 may include a luer-style fitting or other suitable feature for interfacing, but not necessarily connecting, target confirmation device 26 with outer cannula 24.

Distal end 46 of target confirmation device 26 is generally rounded to facilitate entry into the patient's body. In an embodiment, a portion of target confirmation device 26 is configured with a magnetic resonance imaging (MRI) identifiable material, such as inconel 625, titanium or other material with similar magnetic characteristics. In one particular configuration, a targeting band 48 is provided a distance "C" from connecting end 44, as shown in FIG. 3; the distance C being measured from the approximate center of targeting band 48 to connecting end 44 (or the inside of cap 47), for example. Targeting band 48 provides a reference point in an MR image relative to the target biopsy tissue.

In another embodiment of the present invention, the tip of target confirmation device itself may be used to provide the reference point in the MR image, provided the target confirmation device material exhibits a relatively low artifact, or alternatively provides a signal void, during MR imaging. As used herein, the term "artifact" describes a material's tendency to distort an MR image. The term "signal void" describes the absence of signal, generally presented as a dark area in the MR image. A material exhibiting a relatively high artifact will render the adjacent body tissue unreadable in an MR image. Conversely, a material with a relatively low artifact will allow the material to be readily identified in the MR image and will not significantly distort the MR image of the adjacent tissue. Alternatively, a material providing a signal void will not significantly distort the MR image. In addition to materials providing a low artifact or a signal void, the target confirmation material may include any material exhibiting properties that provide for a contrasting image region against the adjacent tissue. Thus, the contrasting image region provides a reference point in an imaging modality relative to the target biopsy site. Indeed, the target confirmation material may be chosen based on performance requirements and context of use including, but not limited to, imaging modality (or modalities, if the target confirmation material may be used with multiple modalities), artifact properties, signal void properties, contrast requirements, and expected adjacent tissue properties (e.g., soft tissue, muscle tissue, brain tissue, tissue density, etc.) Further, the target confirmation material may be selected to provide intermediate levels of artifact and/or signal void.

Figure 3A:
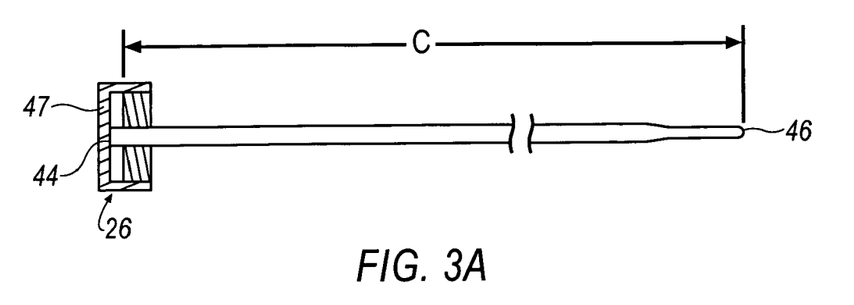
FIGS. 3A and 3B are side views of a target confirmation device according to alternate embodiments of the present invention.
Figure 3B:
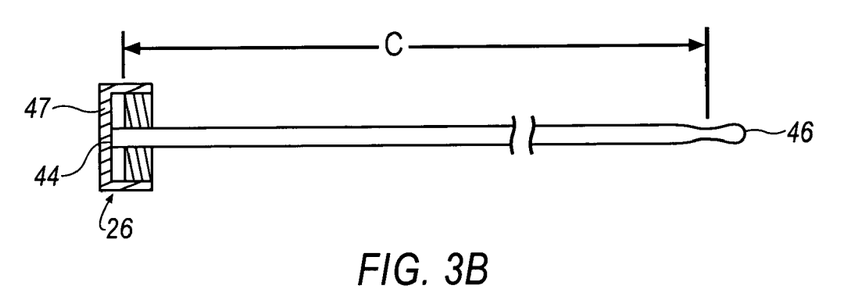

As shown in the embodiments of FIGS. 3A and 3B, the distal end 46 of target confirmation device 26 may include a particular shape to help identify the location of target confirmation device 26 relative to the surrounding tissue. In the embodiment of FIG. 3A, a portion of target confirmation device 26 adjacent the distal end 46 has a smaller diameter relative to the remaining length. In the embodiment of FIG. 3B, a portion of target confirmation device 26 is tapered to provide an hour glass like image when viewed under MR. It will be appreciated that the embodiments represented in FIGS. 3A and 3B are not limited to the configurations shown, and that other configurations are with in the scope of the present invention.

In still another embodiment, introducer stylet 22 may function as a target confirmation device. In this embodiment, introducer stylet 22, and more particularly stylet 30, may be made of an MRI compatible material that preferably, but not necessarily, exhibits a relatively low artifact or a signal void.

Figure 4:
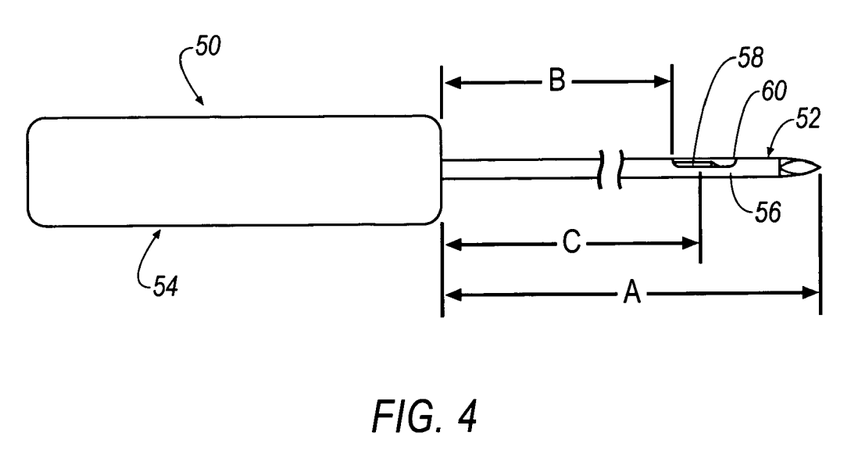
FIG. 4 is a side view of an exemplary biopsy device for use with the introduction system of the present invention.
Figure 5:
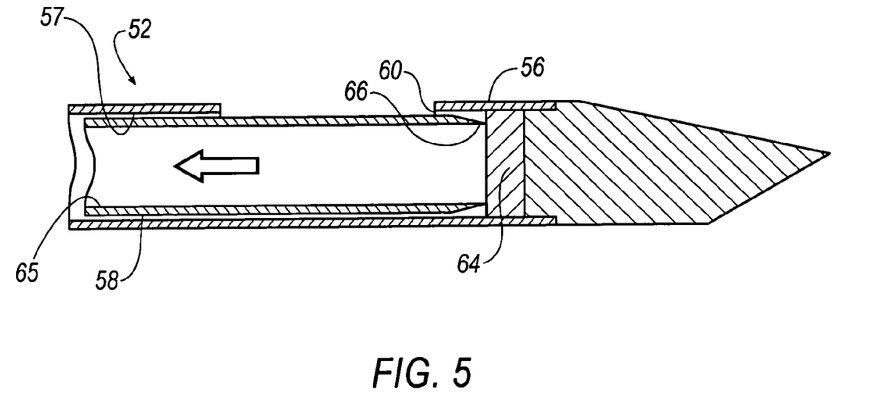
FIG. 5 is a detailed cross-sectional view of a cutting element of the biopsy device of FIG. 4.

An exemplary biopsy apparatus 50, which is suitable for use with medical system 20 of the present invention, is generally shown in FIG. 4 and in more detail in FIG. 5. Apparatus 50 includes a cutting element 52 sized for introduction into the patient's body and a hand piece 54. The exemplary biopsy apparatus 50 is configured as a "tube-within-a-tube" cutting device. More particularly, cutting element 52 includes an outer cannula 56 having an outer lumen 57 and an inner cannula 58 sized to fit concentrically within the outer lumen. A motor or other motion generating device is provided within hand piece 54 to rotate and/or translate inner cannula 58 within outer cannula 56. Biopsy apparatus similar to apparatus 50 can be seen by way of example in pending U.S. patent application Ser. Nos. 09/707,022 and 09/864,03, which are owned by the assignee of the present invention and are incorporated herein by reference in their entirety.

A particular embodiment of the working end of cutting element 52 is depicted in FIG. 5. In the illustrated embodiment, outer cannula 56 defines a tissue-receiving opening 60, which communicates with outer lumen 57. The working end of cutting element 52 further includes a cutting board 64 that is disposed within outer lumen 57 at the distal end of outer cannula 56. Inner cannula 58 defines an inner lumen 65 that is hollow along its entire length to provide for aspiration of the biopsy sample (tissue). Inner cannula 58 terminates in a cutting edge 66 that may be formed by an inwardly beveled surface having a razor-sharp edge.

Figure 6:
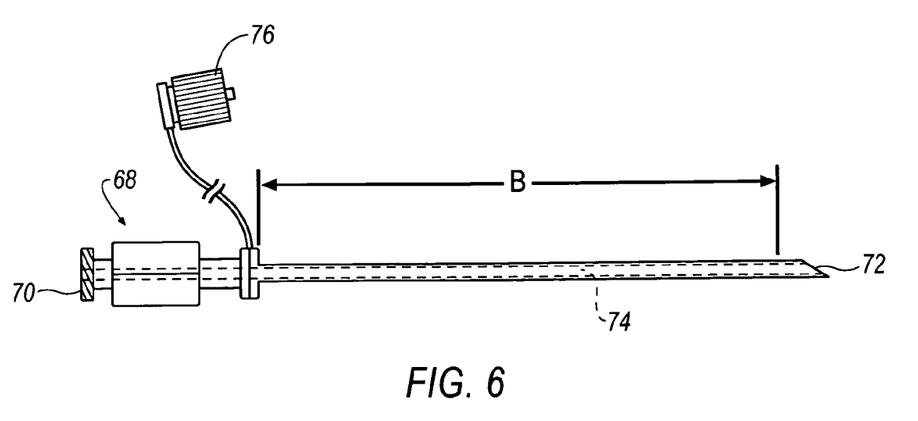
FIG. 6 is a side view of an aspiration wand suitable for insertion into the outer cannula.

Referring to FIG. 6, an wand 68 is shown that can be inserted into outer cannula 24. In an embodiment, wand 68 extends from a connecting end 70 to an insertion end 72 and includes an inner lumen 74 that extends from connecting end 70 to insertion end 72. Connecting end 70 may include a luer interface or other suitable fitting for connecting wand 68 to a vacuum source (not shown). Wand 68 may also include a cap 76 that can be placed onto connecting end 70 to inhibit fluid leakage when wand 68 is inserted into the patient. The haemostatic valve 41 in outer cannula 24 seals against wand 68, as it does against target confirmation device 26 and biopsy device 50, when inserted into outer cannula 24. Additionally, the outside diameter of wand 68 is less than the inside diameter of inner lumen 40 to allow saline or other fluids introduced through fluid conduit 40 to pass into the patient's body. When cap 76 is removed and wand 68 is connected to a vacuum source, fluids, such as blood and saline, can be aspirated from the biopsy site.

Referring to FIGS. 7-11, a medical procedure using system 20 of the present invention will be described. In an embodiment, system 20 is employed to conduct a biopsy of a lesion within a patient's body. The target tissue or lesion to be biopsied and/or removed from the patient's body (denoted generally by mass 80 in FIG. 7) is located using a medical imaging system, such as MRI or other suitable imaging modality. A reference structure 82 may be positioned adjacent the patient to assist in locating the target tissue. The location of the target tissue 80 relative to reference structure 82 may be determined along one or more axis. In the illustrated embodiment, the target tissue location relative to reference structure 82 is determined along the X and Y axes; however, the target tissue location may also be determined along all three of the X, Y and Z axes. While the described method employs a reference structure 82 to locate the target tissue, the reference structure is not necessarily required and a more "free-hand" approach may be utilized.

Figure 7:
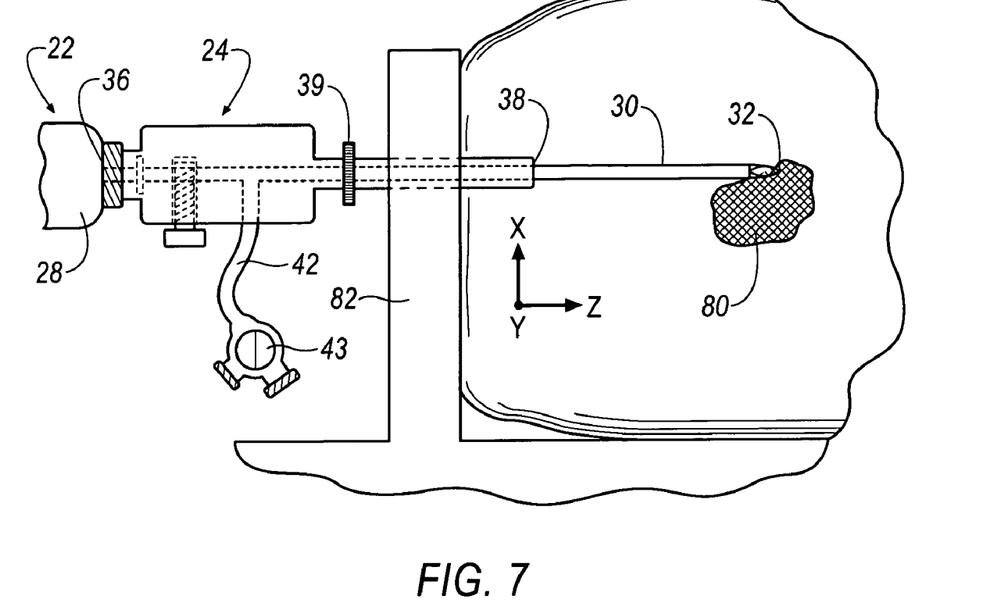
FIGS. 7-11 are elevational views illustrating a medical procedure using the medical system of the present invention.

In an embodiment, reference structure 82 includes a support grid having a number of holes therethrough. Each hole is sized to allow passage of outer cannula 24. The hole through which outer cannula 24 is ultimately inserted is determined by the location of target tissue 80 relative to reference structure 82 along the X and Y axes. The patient and reference structure 82 are viewed using a medical imaging system, such as MRI, to determine the location of the target tissue relative to reference structure 82.

After application of anesthesia, the stylet portion of introducer stylet 22 and a portion of outer cannula 24 are inserted through the support grid and into the patient's body, creating a pathway 84 to the target tissue 80 (see, e.g., FIG. 7). Introducer stylet 22 is then removed from the patient's body leaving behind outer cannula 24 (see, e.g., FIG. 8).

Fluids may be inserted into or removed from the patient's body through inner lumen 40 via fluid conduit 42. These fluids may include, for example, additional anesthetics and/or saline solution to cleanse pathway 84 and remove blood. Accumulated blood and other fluids within pathway 84 may be aspirated through fluid conduit 42 or by inserting wand 68 prior to insertion of target confirmation device 26.

Figure 8:
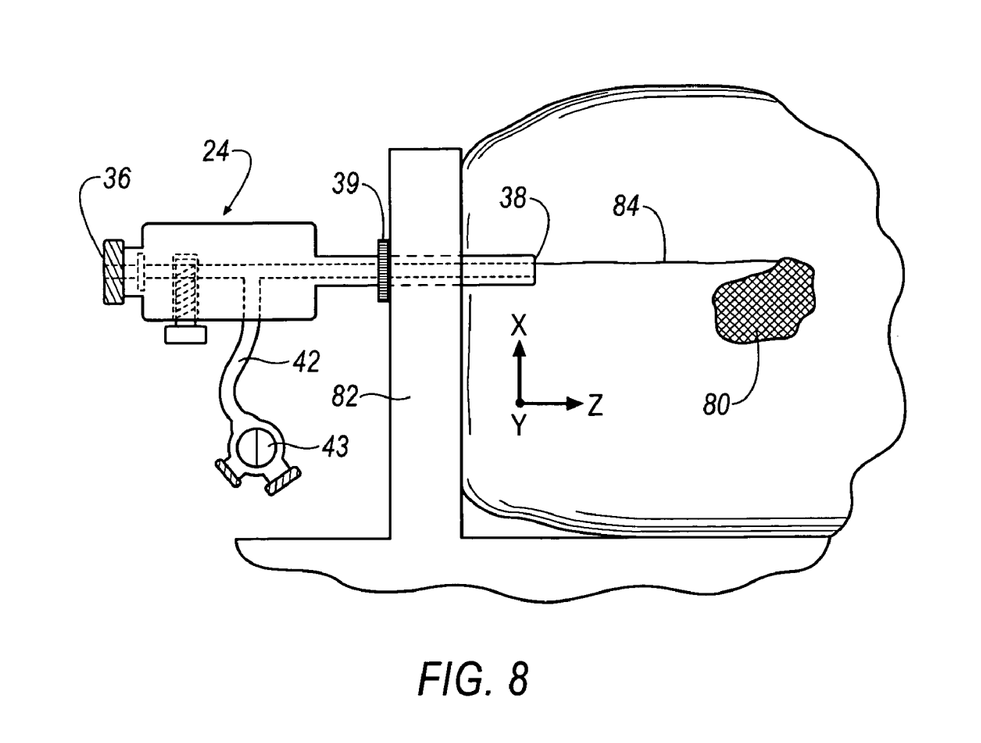
Figure 9:
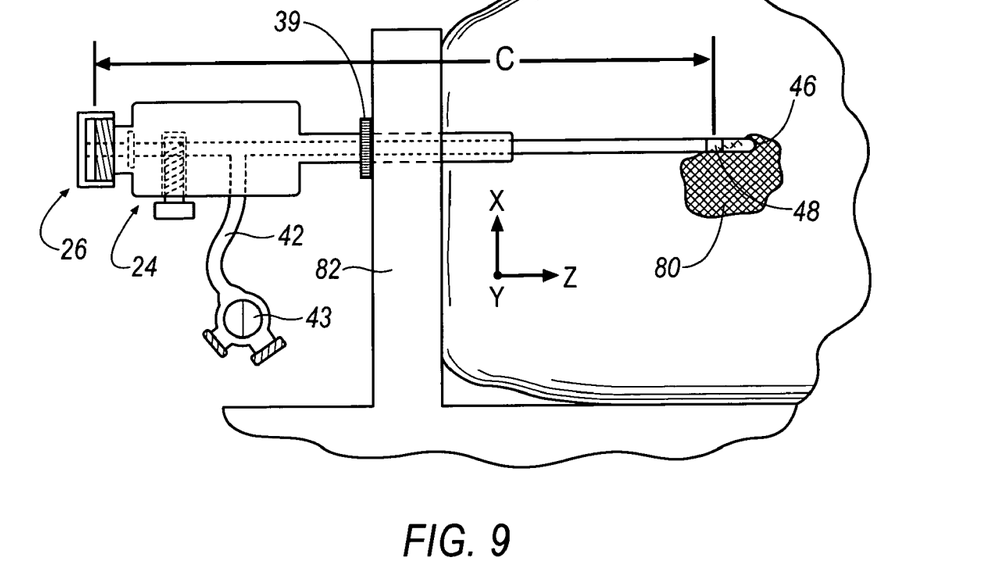
Figure 10:
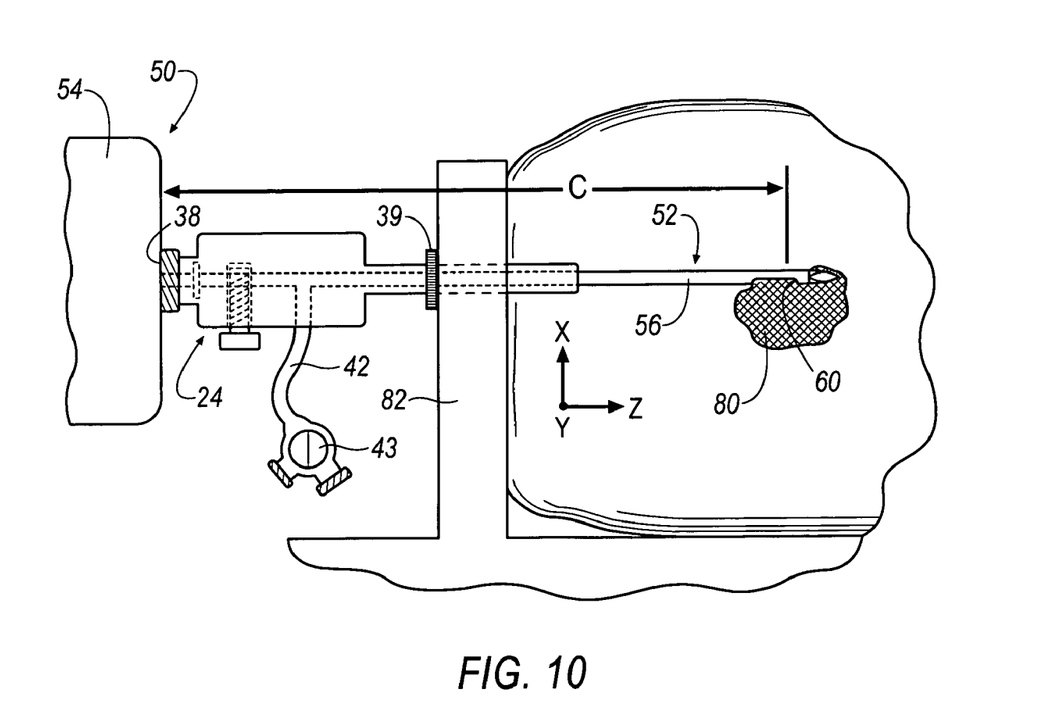

Once introducer stylet 22 is removed from outer cannula 24, target confirmation device 26 may be inserted into the patient's body through the port created by outer cannula 24 (see, e.g., FIGS. 8 and 9). With target confirmation device 26 properly inserted into outer cannula 24, an image of the target site is again taken to determine the location of targeting band 48 in relation to the target tissue and reference structure 82. If targeting band 48 is in the desired position adjacent target tissue 80 along the Z-axis, targeting device 26 is removed from outer cannula 24. However, if targeting band 48 is not in the desired position, then the position of target confirmation device 26 and outer cannula 24 is modified along the Z-axis until the desired position is achieved.

Once the desired position is achieved, depth limiting member 39 is moved against reference structure 82 to inhibit movement of outer cannula 24 further into the patient. When no reference structure 82 is used, depth limiting member may be moved directly against the patient's skin. Target confirmation device 26 is then removed from outer cannula 24 and biopsy device 50 is inserted into outer cannula 24 until handpiece 54 abuts proximal end 36 of outer cannula 24. In the embodiment illustrated in FIG. 10, one or more samples of target tissue 80 are removed from the patient through tissue-receiving opening 60. The correct position of tissue-receiving opening 60 is ensured because the distance "C" between proximal end 44 of target confirmation device 26 and targeting band 48 (see, e.g., FIGS. 3 and 9), or the distance between proximal end 44 and the predetermined location on target confirmation device 26 (FIGS. 3A and 3B), is approximately equal to the distance between the center of tissue receiving opening 60 and handpiece 54 of biopsy device 50.

Figure 11:
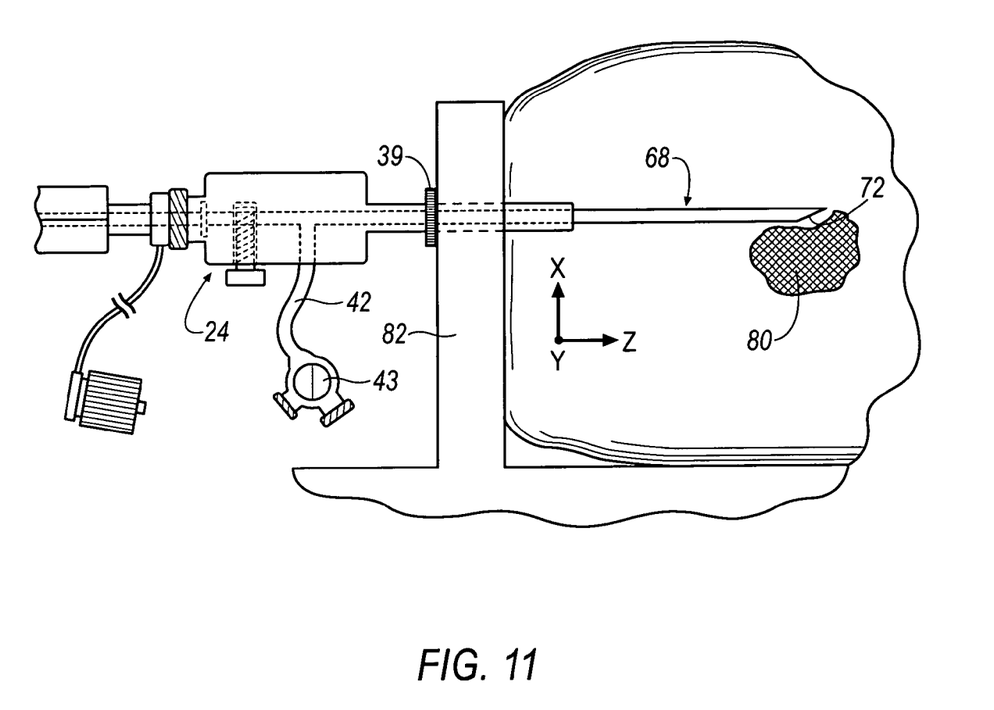

After completion of the biopsy, the biopsy site can be aspirated using wand 68 (see, e.g., FIG. 11). During or after aspiration, a final image of the biopsy site can be taken to confirm removal of the target tissue. Finally, an MRI identifiable marker, such as a collagen plug, or other medical treatment can be inserted into the biopsy site through outer cannula 24.

Among other features, the medical system of the present invention localizes the target biopsy site in a manner that allows confirmation of the target biopsy site under MRI or other visualization modality, and allows positioning of a biopsy device to ensure the cutting element of the biopsy device can be accurately placed at the target biopsy site. The medical system of the present invention also facilitates the introduction and removal of fluids from the target site, including without limitation, anesthesia and blood, but minimizes the exposure of the fluids to the adjacent equipment and medical staff. In addition to allowing the medical staff to identify the presence of significant bleeding and to introduce a biopsy device into the patient, the medical system provides access to the target site to introduce a medical treatment, such as a site marker, tamponade or other haemostatic agent, after removal of the tissue.

The present invention has been particularly shown and described with reference to the foregoing embodiments, which are merely illustrative of the best modes for carrying out the invention. It should be understood by those skilled in the art that various alternatives to the embodiments of the invention described herein may be employed in practicing the invention without departing from the spirit and scope of the invention as defined in the following claims. It is intended that the following claims define the scope of the invention and that the method and apparatus within the scope of these claims and their equivalents be covered thereby. This description of the invention should be understood to include all novel and non-obvious combinations of elements described herein, and claims may be presented in this or a later application to any novel and non-obvious combination of these elements. Moreover, the foregoing embodiments are illustrative, and no single feature or element is essential to all possible combinations that may be claimed in this or a later application.

What is claimed is:

1. A medical targeting and device introduction system, comprising:
   an introducer cannula having an open distal end and an open proximal end that defines a first length, wherein the introducer cannula defines a lumen therein;
   a generally linear introducer stylet that includes a distal end and a proximal end which defines a second length that is substantially longer than the first length; wherein the introducer stylet is selectively and removably disposed within the lumen of the introducer cannula through the open proximal end such that the introducer stylet may be translated within the lumen such that the distal end of the introducer stylet extends outwardly from the distal end of the introducer cannula when the introducer stylet is positioned within the introducer cannula, wherein the distal end of the introducer stylet further includes a tissue piercing tip that is configured for penetrating tissue to create a pathway; and a separate target confirmation device that is selectively insertable within the introducer cannula only when the introducer stylet is removed from the introducer cannula, wherein the target confirmation device includes a distal end that extends substantially outwardly from the distal end of the introducer cannula when the target confirmation device is engaged with the introducer cannula; and a biopsy device that includes a handpiece, an outer cannula and an inner cannula disposed within the outer cannula;

wherein the biopsy device is configured to at least translate the inner cannula within the outer cannula and the inner cannula includes a cutting edge at its distal end, wherein the outer cannula defines a tissue-receiving opening for receiving tissue from the target site, wherein the cutting edge of the inner cannula cooperates with the tissue-receiving opening to sever tissue; and wherein at least a portion of the outer cannula of the biopsy device is selectively insertable within the introducer cannula after the introducer stylet and target confirmation device are removed from the introducer cannula.

2. The system of claim 1, wherein the introducer cannula is configured to introduce at least one of a biopsy device, a site marker, an anesthesia, a fluid, a tamponade, and a hemostatic agent.

3. The system of claim 1, wherein the target confirmation device includes a magnetic resonance imaging (MRI) identifiable material.

4. The system of claim 3, wherein the magnetic resonance imaging (MRI) identifiable material is a band disposed proximate the distal end of the target confirmation device so as to extend distally of the distal end of the introducer cannula.

5. The system of claim 4, wherein the distance between a proximal end of the target confirmation device and the targeting band is approximately equal to the distance between the center of the tissue receiving opening and the handpiece of the biopsy device.

6. The system of claim 1, wherein the system is magnetic resonance imaging (MRI) compatible.

7. The system of claim 1, wherein the outer cannula includes a fluid conduit for delivering fluid provided in communication with the lumen.

8. The system of claim 7, wherein the fluid conduit includes a directional valve.

9. The system of claim 1, wherein the target confirmation device includes a proximal end having a first fitting interface that engages and connects to a second fitting interface on the introducer cannula upon insertion of the target confirmation device into the introducer cannula so as to prevent relative movement between the target confirmation device and the introducer cannula.

10. The system of claim 1, wherein the introducer cannula includes a hemostatic valve.

11. The system of claim 1, wherein the target confirmation device includes a relatively low artifact generating material sufficient to permit the material to be readily identified under magnetic resonance imaging (MRI).

12. The system of claim 1, wherein the target confirmation device has a proximal end, and the distance between the proximal end and the distal end of the target confirmation device is approximately equal to the distance between the center of the tissue receiving opening of the outer cannula and the handpiece of the biopsy device.

13. The system of claim 1, wherein the length of the outer cannula is approximately equal to the length of the introducer stylet.

14. The system of claim 1, wherein the length of the target confirmation device is approximately equal to the length of the introducer stylet.

15. The system of claim 1, wherein said tissue receiving opening is rotatable relative to said introducer cannula.

16. The system of claim 1, wherein the target confirmation device is a low artifact generating material.

17. The system of claim 1, wherein the target confirmation device provides a low artifact.

18. The system of claim 1, wherein the target confirmation device is a signal void generating material.

19. The system of claim 1, wherein the target confirmation device provides a signal void.

20. The system of claim 1, wherein the length of the target confirmation device is approximately equal to the length of the outer cannula.

21. A biopsy system suitable for use with a magnetic resonance imaging (MRI) device, comprising:

an introducer cannula insertable into a patient's tissue, wherein the introducer cannula includes an open distal end and an open proximal end and wherein the introducer cannula defines a first length;

an introducer stylet removably disposed within the introducer cannula and configured for tissue penetration and slidable within the introducer cannula, wherein the introducer stylet includes a distal end and a proximal end, and wherein the introducer stylet defines a second length that is substantially longer than the first length such that when the introducer stylet is fully inserted into the introducer cannula, the distal end of the introducer stylet extends through the distal end of the introducer cannula and substantially away from the distal end of the introducer cannula;

a separate target confirmation device that is selectively insertable within the introducer cannula, wherein the target confirmation device includes a distal end that extends substantially outwardly from the distal end of the introducer cannula when the target confirmation device is engaged with the introducer cannula; wherein the target confirmation device further includes a magnetic resonance imaging (MRI) identifiable material disposed adjacent to the distal end thereof such that the material is positioned outwardly from the distal end of the introducer cannula when the target confirmation device is positioned within the introducer cannula; and a separate biopsy device having an outer cannula and an inner cannula disposed within the outer cannula, wherein the inner cannula of the biopsy device includes a cutting edge for severing tissue and the outer cannula of the biopsy device is sized for selective insertion within the introducer cannula through the open proximal end when the introducer stylet and target confirmation device are removed from the introducer cannula.

22. The system of claim 21, wherein the introducer cannula is configured to introduce at least one of a site marker, an anesthesia, a fluid, a tamponade and a hemostatic agent into the patient.

23. The system of claim 21, wherein the distal end of the target confirmation device has a predetermined shape so as to distinguish the target confirmation device from the patient's tissue.

24. The system of claim 21, wherein the magnetic resonance imaging (MRI) identifiable material is a band disposed proximate the distal end of the target confirmation device.

25. The system of claim 21, wherein the biopsy system is magnetic resonance imaging (MRI) compatible.

26. The system of claim 21, wherein said biopsy device includes a tissue receiving opening positioned in a sidewall of the outer cannula adjacent a distal end thereof, and said tissue receiving opening is rotatable relative to said introducer cannula.

27. The system of claim 21, wherein the outer cannula has a tissue receiving opening.

28. A medical procedure, comprising:
inserting an introducer stylet into an outer cannula such that a distal end of the introducer stylet extends substantially outwardly from a distal end of the outer cannula;
inserting the introducer stylet, with the outer cannula disposed thereon, into a patient's body, thereby creating a pathway to a target tissue;
removing the introducer stylet from the patient's body, but leaving behind the outer cannula; and
inserting a separate target confirmation device into the patient's body through the outer cannula such that a distal end of the target confirmation device extends substantially outwardly from the distal end of the outer cannula and confirming the location of the target tissue relative to the target confirmation device.

29. The method of claim 28, further including the step of providing an image of the target tissue prior to or contemporaneous with inserting the introducer stylet into the patient's body.

30. The method of claim 28, further including the step of providing an image of the target confirmation device within the patient's body.

31. The method of claim 28, further including the step of removing the target confirmation device and inserting a biopsy device through the outer cannula to a position adjacent the target tissue.

32. The method of claim 31, further including the step of performing a biopsy of the target tissue.

33. The method of claim 32, further including the step of aspirating a biopsy site formed after removing the target tissue.

34. The method of claim 33, further including the step of inserting a medical treatment into the biopsy site through the outer cannula.

35. The method of claim 28, further including the step of providing an image of the target tissue after inserting the introducer stylet into the patient's body.

36. The method of claim 28, further including removing the target confirmation device and inserting a biopsy device including a tissue receiving opening into the outer cannula, wherein said tissue receiving opening is selectively rotatable relative to said outer cannula.

37. A breast biopsy system for use with a magnetic resonance imaging (MRI) device, comprising:
a first introducer cannula insertable into a patient's breast tissue, wherein the first introducer cannula has a single lumen and defines an open distal end and an open proximal end;
a unitary introducer and target confirmation stylet that is slidable in a distal direction into and along the single lumen of the first introducer cannula and which is slidably removable therefrom in a proximal direction, wherein the introducer and target confirmation stylet includes a distal end having a piercing tip configured for breast tissue penetration and a proximal end, and wherein at least a portion of the piercing tip of the introducer and target confirmation stylet extends in the distal direction through and beyond the distal end of the first introducer cannula into a first relative position between the first introducer cannula and the introducer and target confirmation stylet;
wherein at least one of the first introducer cannula and the introducer and target confirmation stylet includes a magnetic resonance imaging (MRI) compatible material that is visible under MRI imaging; and
a breast tissue biopsy device that is slidably insertable in the distal direction within the single lumen of the first introducer cannula through the open proximal end only after the introducer and target confirmation stylet is removed in the proximal direction from the first introducer cannula, wherein the biopsy device comprises a handpiece, a second outer cannula and a third inner cutting cannula, and wherein the third inner cutting cannula is rotatable and translatable within the second outer cannula and the second outer cannula has a tissue receiving opening, the third inner cutting cannula has a lumen, and the lumen of the third inner cutting cannula selectively communicates with the tissue receiving opening to excise tissue adjacent the tissue receiving opening of the second outer cannula when the second outer cannula is inserted into a patient's breast tissue.

38. A medical procedure, comprising:
locating a target tissue area in a patient's breast using a magnetic resonance imaging (MRI) system;
providing a unitary introducer and target confirmation stylet having a tissue piercing tip at a distal end thereof and comprising a magnetic resonance imaging compatible material;
inserting the introducer and target confirmation stylet through a first introducer cannula having an open distal end such that the piercing tip of the introducer and target confirmation stylet extends at least partially through the open distal end of the first introducer cannula;
inserting the introducer and target confirmation stylet with the first introducer cannula disposed thereon into a patient's body such that the tissue piercing tip of the introducer and target confirmation stylet enters the patient's breast prior to the distal end of the first introducer cannula and moving the introducer and target confirmation stylet with the first introducer cannula thereon through the patient's breast tissue to create a pathway to a target tissue;
imaging at least a distal end of the introducer and target confirmation stylet while the introducer and target confirmation device is positioned within the patient's breast to confirm the location of the introducer and target confirmation stylet relative to the target tissue;
slidably removing the introducer and target confirmation stylet from the patient's breast, thereby leaving behind the first introducer cannula such that the distal end of the first introducer cannula remains positioned within the patient's breast;
providing a biopsy device comprising a handpiece, a second outer cannula, and a third inner cutting cannula, wherein the second outer cannula has a proximal end and a distal end, the proximal end of the second outer cannula is located proximal the handpiece, and the tissue receiving opening is located adjacent the distal end of the second outer cannula, and wherein the third inner cutting cannula has a proximal end, a distal end, a cutting edge formed on the distal end, a lumen, and is selectively rotatable and translatable within the second outer cannula such that the tissue receiving opening of the second outer cannula selectively communicates with the lumen of the third inner cutting cannula;

inserting the second outer cannula of the biopsy device within the first introducer cannula such that the tissue receiving opening of the second outer cannula extends through the open distal end of the first introducer cannula when the introducer and target confirmation stylet is removed from the first introducer cannula; and positioning the tissue receiving opening of the second outer cannula in a selected relative position with respect to the target tissue to allow a portion of the target breast tissue to prolapse into the tissue receiving opening; moving the third inner cutting cannula distally within the second outer cannula while rotating the third inner cutting cannula relative to the second outer cannula until the cutting edge extends beyond the tissue receiving opening, thereby cutting a portion of the breast tissue that has prolapsed into the tissue receiving opening.

* * * * *